United States Patent [19]

Neiss et al.

[11] Patent Number: 4,746,676
[45] Date of Patent: May 24, 1988

[54] CARBOXYALKYL DIPEPTIDE COMPOUNDS

[75] Inventors: Edward S. Neiss, New Canaan; John T. Suh, Greenwich, both of Conn.; John R. Regan, Mamaroneck, N.Y.; Jerry W. Skiles, Tuckahoe, N.Y.; Jeffrey N. Barton, New York, N.Y.; Paul Menard, Tuckahoe, N.Y.

[73] Assignee: Rorer Pharmaceutical Corporation, Fort Washington, Pa.

[21] Appl. No.: 649,797

[22] Filed: Sep. 12, 1984

[51] Int. Cl.$^4$ .................. A61K 31/40; C07D 207/14
[52] U.S. Cl. ............................ 514/423; 514/259; 514/307; 544/12; 544/13; 544/287; 546/117; 548/483; 548/517; 548/533
[58] Field of Search .................. 548/483, 517, 533; 544/12, 13, 287; 514/259, 307, 423

[56] References Cited

U.S. PATENT DOCUMENTS

| | | | |
|---|---|---|---|
| 4,293,481 | 10/1981 | Condon et al. | 548/532 |
| 4,374,829 | 2/1983 | Harris et al. | 514/21 |
| 4,431,644 | 2/1984 | Smith et al. | 548/533 |
| 4,442,030 | 4/1984 | Greenlee | 530/800 |
| 4,524,212 | 6/1985 | Gordon et al. | 548/533 |
| 4,558,037 | 12/1985 | Chan et al. | 514/20 |

FOREIGN PATENT DOCUMENTS 88350  9/1983  European Pat. Off. .

Primary Examiner—Glennon H. Hollrah
Assistant Examiner—James H. Turnipseed

[57] ABSTRACT

Compounds having the general structure

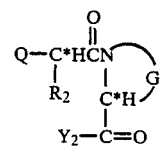

and their pharmaceutically acceptable salts, wherein the substituents are defined herein, which exhibit antihypertensive activity.

10 Claims, No Drawings

CARBOXYALKYL DIPEPTIDE COMPOUNDS

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula (1)

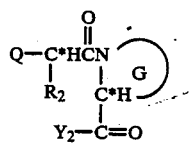

and its pharmaceutically acceptable acid addition, alkali and alkaline earth metal salts, wherein Q is $Y_1$—C(O)—C*H($R_1$)NH—, —$NH_2$, $R_1$—C(O)S(C*H($R_1$))$_{0-1}$—, or HS—(C*H($R_1$))$_{0-1}$;

$Y_1$ and $Y_2$ are independently —OH, —OR, or —$NR_1R_2$;

G is

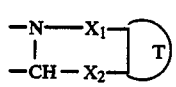

in which $G_1$ is H, —OH, $C_{1-6}$ alkyl, or $C_{1-6}$ alkoxy, $X_1$ and $X_2$ are independently a chemical bond or an alkylene bridge 1, 2 or 3 carbon atoms in length, provided that the ring which contains $X_1$ and $X_2$ contains 4 to 6 carbon atoms; one or both of $X_1$ and $X_2$ is optionally substituted with —OH, $C_{1-6}$ alkyl, or $C_{1-6}$ alkoxy; one of $X_1$ and $X_2$ is substituted with Z; $X_1$ and $X_2$ are otherwise substituted with hydrogen; and T is a saturated, unsaturated, or aromatic, hydrocarbon ring with 5 to 7 carbon atoms;

Z is =CH—(CH$_2$)$_i$C(O)M, —(CH$_2$)$_i$C(O)M, —(CH$_2$)$_i$—N(R$_3$)—C(O)—M, —(CH$_2$)$_i$C(O)—N(R$_3$M, —(CH$_2$)$_i$SO$_2$M, —(CH$_2$)$_i$N(R$_3$)M, —O(CH$_2$)$_i$C(O)M, —(CH$_2$)$_i$—N(R$_3$)—SO$_2$—M, —(CH$_2$)$_i$M, —N(R$_3$)M, —N(R$_3$)—CH$_2$(CH$_2$)$_i$N(R$_3$)M, —O(CH$_2$)$_i$M, =N(CH$_2$)$_i$SO$_2$M, =N(CH$_2$)$_i$M, =CH(CH$_2$)$_i$M, or —CH$_2$=CHM, wherein i is 0 to 6 inclusive provided that one carbon atom of a —(CH$_2$)$_i$-linkage can be substituted with a straight or branched-chain alkyl group of up to 3 carbon atoms;

M is

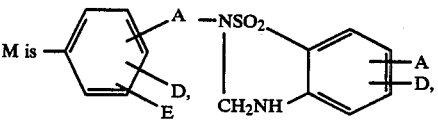

-continued

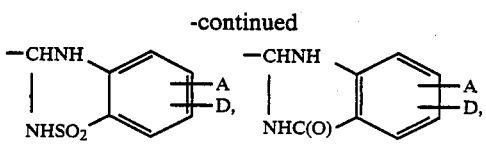

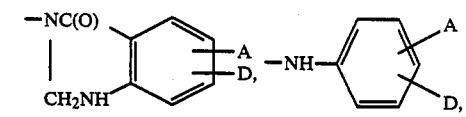

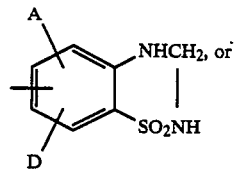

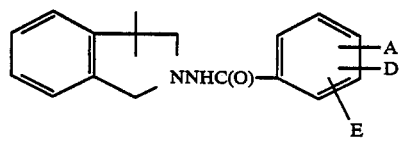

wherein

A, D and E are independently H, $C_{1-6}$ alkyl, phenyl, benzyl, phenoxy, nitroalkylamino, alkanoylamino, alkanoylaminoalkyl, nitro, —OCH$_2$COOH, halogen, hydroxy, —CF$_3$, —SR, —OR, —NR$_1$R$_2$, —C(O)NR$_1$(R$_2$), —C(O)Y$_1$, —SO$_2$R, —SO$_2$NR$_1$R$_2$, or furfurylamino, provided that neither A nor D is hydrogen; and R, R$_1$, R$_2$, and R$_3$ in each occurrence, are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, fused cycloalkylaryl having 8 to 12 carbon atoms, heterocyclic, or an alkyl group having 1 to 6 carbon atoms which is substituted with —NH$_2$, —NH—C(NH$_2$)=NH, or

wherein the alkyl, cycloalkyl, aryl, and fused aryl-cycloalkyl groups may carry substituents selected from the group consisting of alkoxy with 1 to 6 carbon atoms, —CF$_3$, —OH, —SH, halogen, —NO$_2$, and —COOR.

DETAILED DESCRIPTION OF THE INVENTION

Preferred substituents within the scope of the present invention include those wherein $Y_1$ and $Y_2$ are independently hydroxy or alkoxy containing up to 8 carbon atoms;

$R_1$ is H; alkyl having 1 to 8 carbon atoms; phenyl-alkyl wherein the alkyl has 1 to 4 carbon atoms, and more preferably phenethyl; or indanyl, e.g. 2-indanyl;

$R_2$ is H; alkyl having 1 to 8 carbon atoms; or an alkyl group having 1 to 8 carbon atoms, which is substituted with amino or an amino derivative such as —NH—C(NH$_2$)=NH, or

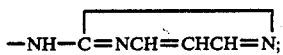

and R₂ is more preferably —CH₃ or NH₂(CH₂)₄—.

In the preferred embodiment, ring G is proline, or a proline ring containing one C=C double bond. In a preferred embodiment when G forms a fused ring system, $X_1$ and $X_2$ and T form tetrahydroquinoline or tetrahydroisoquinoline, or $X_1$ and $X_2$ form a proline ring. The proline ring of the one-ring or two-ring system G is preferably unsubstituted or substituted with an $R_3$ group which is preferably —OH or alkyl containing 1 to 6 carbon atoms.

When the chain connecting the moiety M to the ring includes a —(CH₂)ᵢ-linkage where i is non-zero, one of the carbon atoms of that linkage can be substituted with a straight-chained or branched alkyl group of up to 6 carbon atoms. Preferred connecting chains include those attached at the ring G by a double bond; —NH—; —NHSO₂; —NHC(O); and —CH₂NHC(O).

A is preferably —NH₂; —OH; —OCH₂COOH; phenoxy; furfurylamino; alkoxy having up to 6 carbon atoms; or —SO₂NR₁R₂ wherein $R_1$ and $R_2$ are hydrogen, methyl, or $C_{2-3}$ alkyl, and more preferably —SO₂NH₂.

D is preferably halogen, and more preferably chloro; —CF₃; or —SO₂NR₁R₂ wherein $R_1$ and $R_2$ are hydrogen, methyl, or $C_{2-3}$ alkyl, and more preferably —SO₂NH₂; and E is preferably halogen or hydrogen.

The alkyl groups in general include straight-chained and branched groups, including methyl, ethyl, propyl, isopropyl, butyl, isobutyl, tert-butyl, amyl, iso-amyl, hexyl, and the like. By "halogen" is meant chloro, bromo, iodo, and fluoro.

Preferred substituents for $R_1$ and/or $R_2$ also include cycloalkyl groups, aryl groups, heterocyclic groups, and fused aryl-cycloalkyl groups, as defined herein. The preferred cycloalkyl groups include cyclopropyl, cyclobutyl, cyclopentyl, cyclohexyl, cycloheptyl, adamantyl, or norbornyl. The preferred aryl and fused aryl-cycloalkyl groups include phenyl, indolyl, indolinyl, indanyl, naphthyl, tetrahydronaphthyl, and decahydronaphthyl. Preferred heterocyclic groups include pyridyl, quinolyl, isoquinolyl, tetrahydroquinolyl, tetrahydroisoquinolyl, decahydroquinolyl, decahydroisoquinolyl, pyrrolidyl, pyrrolyl, morpholinyl, furyl, tetrahydrofuryl, furfuryl, benzimidazolyl, thienyl, and imidazolyl. Preferred aryl-alkyl substituents include benzyl and phenethyl. Preferred substituents on the alkyl, cycloalkyl, aryl, and fused aryl-cycloalkyl substituents include alkyl and alkoxy with 1 to 6 carbon atoms, —CF₃, —OH, —NH₂, phenoxy, —NR₁R₂, —COOH, —CN, —SH, halogen, —NO₂, and COOR, particularly COO—C₁₋₆ alkyl.

Compounds according to formula (1) can contain asymmetric centers at the carbon atoms marked thus: C*. Each of these carbon atoms can have an (R) or an (S) configuration, and preferably (S). Individual optical diastereoisomers as well as mixtures thereof are considered to be within the scope of this invention. When diastereoisomeric products result from the synthetic procedures, the desired diastereoisomeric product can be separated by conventional chromatographic or fractional crystallization methods.

The compounds of formula (1) can be prepared by coupling compounds of formulas (2) and (3)

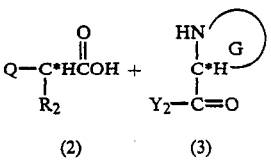

(2)        (3)

in which the substituents on ring G, including Z, are previously present or are subsequently attached. The various substituents on compounds (2) and (3) have been defined above.

It will be recognized by those skilled in this art that the coupling of compounds (2) and (3) can be carried out by conventional peptide linkage techniques, e.g. in the presence of a coupling agent such as DCC (N,N'-dicyclohexylcarbodiimide) or CDI (N,N'-carbonyldiimidazole). Alternatively, one may prefer to convert the —COOH group of compound (2) to —C(O)Cl, and then react the resulting intermediate with compound (3). Alternatively one may preferably convert the compound (2) to the corresponding N-carboxyanhydride (NCA) by allowing (2) to react with phosgene, and then react the resulting N-carboxyanhydride with compound (3) to yield the desired intermediate. It will further be recognized that the nitrogen atom which is between the carbon atoms to which $R_1$ and $R_2$ are attached can be protected with a blocking group such as 2,2,2-trichloroethoxycarbonyl, or benzyloxycarbonyl. The protecting group is subsequently removed, preferably after compounds (2) and (3) have been joined together. Other nitrogen atoms, in substituents such as NH₂(CH₂)₄—, should be protected and then deprotected in a similar manner. Similarly, $Y_1$ and $Y_2$ are preferably converted to ethoxy, t-butoxy, or benzyloxy, before the intermediates are reacted. If the free acid is desired, it is subsequently obtained by removal of the esterifying group in a known manner.

The compounds of the present invention in which one of $Y_1$ and $Y_2$ is —OH and the other is alkoxy, such as methoxy or ethoxy, are preferably made by reacting compounds (2) and (3) as shown above in which one of $Y_1$ and $Y_2$ is the desired alkyl ester, and the other is an easily cleaved ester group such as t-butoxy. The amide intermediate thus prepared yields upon a mild acid hydrolysis the desired monoester-monoacids.

When Q contains sulfur, the preferred synthetic route is via the acid chloride.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, H₂SO₄, H₃PO₄, as well as methanesulfonic, toluenesulfonic, maleic, acetic, malic, citric, fumaric and camphorsulfonic acids. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin -to- angiotensin I -to- angiotensin II sequence inhibit angiotensin I converting enzyme and therefore are useful in reducing or relieving hypertension.

Furthermore, the compounds within the scope of the present invention which possess diuretic activity promote relief from hypertension by promoting diuresis, and consequently have utility in treating congestive heart failure. Compounds within the scope of this invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of this invention are also indicated for use in reducing intraocular pressure, i.e. for treating glaucoma. This effect is obtained by administering the amounts indicated above to a host in need of such treatment.

The compounds of the invention can be utilized by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE 1

N-[N-[(1S)-1-(Hydroxycarbonyl)-3-phenylpropyl]-L-alanyl]-4-(2,4-disulfamoyl-5-chloroanilino)proline A mixture of N-[N-[(1S)-1-(ethoxycarbonyl)-3-phenylpropyl]-N-(2,2,2-trichloroethoxycarbonyl)-L-alanyl]-L-prolin-4-one ethyl ester (2 mmol), 4-amino-6-chloro-N,N'-bis[(dimethylamino)methylene]-1,3-benzenedisulfonamide (3 mmol), sodium cyanoborohydride (5 mmol) and molecular sieves in absolute ethanol is stirred at room temperature for several days, filtered and the volatiles are removed in vacuo. The residue is purified by HPLC. The 2,2,2-trichloroethoxycarbonyl protecting group is removed with zinc and acetic acid and the esters and sulfonamide protecting groups are removed by reaction with alkali to provide the product.

EXAMPLE 2

N-[N-[(1S)-1-(Hydroxycarbonyl)-3-phenylpropyl]-L-alanyl]-4-[[(2-amino-4-chloro-5-sulfamoylphenyl)sulfonyl]amino]proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (1 mmol) and 1-(N-(2,2,2-trichloroethoxycarbonyl)amino)-3-chloro-4,6-benzenedisulfonamide (2 mmol) and molecular sieves in absolute ethanol is added sodium cyanoborohydride (2 mmol) portionwise. The mixture is kept at room temperature for 24 hours and additional sodium cyanoborohydride (2 mmol) is added. The mixture is kept at room temperature 24 hours, filtered and the volatiles are removed in vacuo. Purification of the residue on HPLC and concentration of the product rich fractions provide the intermediate. The 2,2,2-trichloroethoxycarbonyl protecting groups are removed with zinc and acetic acid and the esters are hydrolyzed with alkali to furnish the product.

EXAMPLE 3

N-[N-[(1S)-1-(Hydroxycarbonyl)-3-phenylpropyl]-L-alanyl]-4-(2,4-disulfamoyl-5-chlorophenylimino)proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (20 mmol), 4-amino-6-chloro-N,N'-bis[(dimethylamino)methylene]-1,3-benzenedisulfonamide (35 mmol) and molecular sieves in absolute ethanol is added anhydrous HCl. The mixture is heated at reflux for 24 hours, cooled to room temperature, filtered and the volatiles are removed in vacuo. The residue is purified by HPLC. The intermediate is treated with zinc and acetic acid in ethyl acetate, to remove the 2,2,2-trichloroethoxycarbonyl protecting group, and with alkali, to remove the sulfonamide protecting groups and hydrolyze the esters, thereby providing the product.

EXAMPLE 4

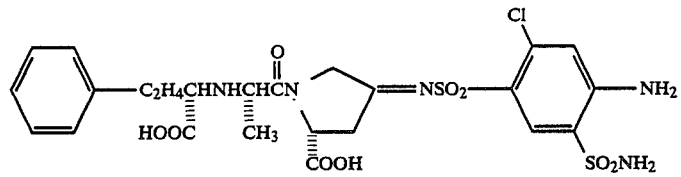

N-[N-[(1S)-1-(Hydroxycarbonyl)-3-phenylpropyl]-L-alanyl]-4-(2-chloro-4-amino-5-sulfamoylphenyl-sulfonylimino)proline To a mixture of N-[N-[(1S)-1-(ethoxycarbonyl)-3-phenylpropyl]-N-(2,2,2-trichloroethoxycarbonyl)-L-alanyl]-L-prolin-4-one ethyl ester (25 mmol), 1-(N-(2,2,2-trichloroethoxycarbonyl)amino)-3-chloro-4,6-benzenedisulfonamide (55 mmol) and molecular sieves in absolute ethanol is added anhydrous HCl. The mixture is heated at reflux overnight, cooled to room temperature, filtered, and the volatiles are removed in vacuo. The residue is purified by HPLC. The 2,2,2-trichloroethoxycarbonyl protecting groups are removed with zinc and acetic acid in ethyl acetate and the esters are hydrolyzed with alkali to give the product.

EXAMPLE 5

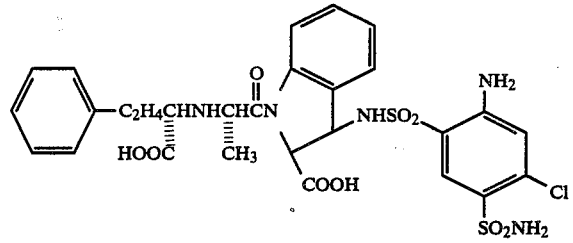

N-[N-[(1S)-1-(Hydroxycarbonyl)-3-phenylpropyl]-L-alanyl]-3-[[(2-amino-4-chloro-5-sulfamoylphenyl)sulfonyl]amino]-2,3-dihydroindole-2-carboxylic acid To a solution of N-[(1S)-1-(ethoxycarbonyl)-3-phenylpropyl]-N-(2,2,2-trichloroethoxycarbonyl)-L-alanine (2 mmol) in methylene chloride at 0° C. is added 1,1'-carbonyldiimidazole (2 mmol). The mixture is stirred 30 minutes and 3-[[(2-(N-2,2,2-trichloroethoxycarbonyl)amino-4-chloro-5-sulfamoylphenyl)sulfonyl]amino]-2,3-dihydroindole-2-carboxylic acid ethyl ester (2.1 mmol) is added. The mixture is warmed to room temperature, stirred overnight, and the volatiles are removed in vacuo. Purification of the residue on HPLC provides the intermediate amide. The 2,2,2-trichloroethoxycarbonyl protecting group is removed with zinc and acetic acid and the esters are hydrolyzed with alkali to provide the product.

EXAMPLE 6

N-[N-[(1S)-1-(Hydroxycarbonyl)-3-phenylpropyl]-L-alanyl]-3-(2,4-disulfamoyl-5-chloroanilino)-2,3-dihydroindole-2-carboxylic acid To a solution of N-[(1S)-1-(ethoxycarbonyl)-3-phenylpropyl]-N-(2,2,2-trichloroethoxycarbonyl)-L-alanine (5 mmol) in methylene chloride at 0° C. is added 1,1'-carbonyldiimidazole (5.5 mmol). The mixture is stirred 30 minutes and 3-(2,4-disulfamoyl-5-chloroanilino)-2,3-dihydroindole-2-carboxylic acid ethyl ester (6 mmol) is added. The mixture is warmed to room temperature, stirred overnight and the volatiles are removed in vacuo. Purification of the residue on HPLC provides the intermediate amide. The 2,2,2-trichloroethoxycarbonyl protecting group is removed with zinc and acetic acid and the esters are hydrolyzed with alkali to provide the product.

EXAMPLE 7

A.

(4S)-1-((2S)-2-(N-((1S)-1-Ethoxycarbonyl-3-phenylpropyl)-N-(2,2,2-trichloroethoxycarbonyl)amino)propionyl)-4-(4-chloro-2-(furfurylamino)-5-sulfonamidobenzoyl)-aminoproline ethyl ester A stirred solution of 11.3 g (0.025 mol) of N-((1S)-1-ethoxycarbonyl-3-phenylpropyl)-N-(2,2,2-trichloroethoxycarbonyl)alanine in 200 ml CH2Cl2 is treated with 5 drops DMF, followed by a solution of 10 ml (0.12 mol) of oxalyl chloride in 50 ml CH2Cl2 added dropwise. The resulting solution is stirred for one hour after gas evolution ceases, then concentrated in vacuo. The residue is redissolved in 100 ml CCl4, decanted from a small amount of red oil, and concentrated again in vacuo.

A solution of 9.4 g (0.020 mol) of (4S)-4-(4-chloro-2-(furfurylamino)-5-sulfonamido-benzoyl)aminoproline ethyl ester and 2.5 g (0.025 mol) triethylamine in 200 ml CH2Cl2 is stirred in an ice bath while a solution of the above acid chloride in 100 ml CH2Cl2 is added dropwise. The mixture is allowed to reach room temperature overnight, then washed with dilute acid and dried. The solution is concentrated in vacuo and chromatographed on silica gel to afford the desired amide.

B.

(4S)-1-((2S)-2-(N-((1S)-1-Ethoxycarbonyl-3-phenylpropyl)amino)propionyl)-4-(4-chloro-2-(furfurylamino)-5-sulfonamidobenzoyl)aminoproline ethyl ester To a solution of 9.4 g (10.5 mmol) of the above acylproline derivative in a mixture of 100 ml EtOH and 50 ml HOAc is added 6.5 g (0.10 mol) zinc dust. The resulting slurry is stirred at room temperature until TLC shows complete disappearance of starting material. Zinc salts and unreacted metal are filtered off and the filtrate concentrated in vacuo. Rapid chromatography on silica gel provides the pure amine.

C.
(4S)-1-((2S)-2-(N-((1S)-1-Carboxy-3-phenylpropyl)amino)propionyl)-4-(4-chloro-2-(furfurylamino)-5-sulfonamidobenzoyl)aminoproline To an ice-cooled solution of 3.5 g (4.79 mmol) of the above diester in 50 ml EtOH is added dropwise 25 ml 1N NaOH. The bath is removed and the solution stirred until TLC indicates complete ester hydrolysis. The solution is carefully neutralized with 1N HCl, then concentrated in vacuo and chromatographed on silica gel to give the desired product.

EXAMPLE 8

A.
(4S)-1-((2S)-2-(N-((1S)-1-Ethoxycarbonyl-3-phenylpropyl)-N-(2,2,2-trichloroethoxycarbonyl)amino)propionyl)-4-(4-amino-2-chloro-5-sulfonamido-benzenesulfonamido)proline ethyl ester A crude acid chloride is prepared from 5.22 g (11.5 mmol) of N-((1S)-1-ethoxycarbonyl-3-phenylpropyl)-N-(2,2,2-trichloroethoxycarbonyl)alanine as described in Example 7A. This is dissolved in 25 ml $CH_2Cl_2$ and added dropwise to an ice-cooled solution of 4.3 g (10.1 mmol) of (4S)-4-(4-amino-2-chloro-5-sulfonamidobenzenesulfonyl)amino-proline ethyl ester and 1.5 g (14.8 mmol) of triethylamine in 150 ml $CH_2Cl_2$. The reaction is stirred overnight at room temperature, then worked up as in Example 7A and chromatographed to give the title amide.

B.
(4S)-1-((2S)-2-(N-((1S)-1-Ethoxycarbonyl-3-phenylpropyl)amino)propionyl)-4-(4-amino-2-chloro-5-sulfonamidobenzenesulfonyl)aminoproline ethyl ester A solution of 4.3 g (5.0 mmol) of product 8A in 50 ml EtOH is treated sequentially with 25 ml HOAc and 4.2 g (66 mmol) of zinc dust. The reaction is stirred at room temperature until complete, as determined by TLC, then worked up as described in Example 7B to provide the desired amine.

C.
(4S)-1-((2S)-2-(N-((1S)-1-Carboxy-3-phenylpropyl)amino)propionyl)-4-(4-amino-2-chloro-5-sulfonamidobenzenesulfonyl)aminoproline A solution of 2.5 g (3.6 mmol) of product 8B in 35 ml EtOH is hydrolyzed with 15 ml 1N NaOH as described in Example 7C. Neutralization and chromatography of the crude product gives the pure diacid.

EXAMPLE 9

A. Ethyl (1S,3S)-1-(4-chloro-3-sulfonamidobenzoylamino)methyl-2-((2S)-N-((1S)-1-ethoxycarbonyl-3-phenylpropyl)-N-(2,2,2-trichloroethoxycarbonyl)amino)-propionyl-1,2,3,4-tetrahydroisoquinoline-3-carboxylate A solution of acid chloride, prepared from 9.5 g (0.021 mol) of N-((1S)-1-ethoxycarbonyl-3-phenylpropyl)-N-(2,2,2-trichloroethoxycarbonyl)alanine as in Example 7A, in 20 ml $CH_2Cl_2$ is added dropwise to an ice-cooled, stirred solution of 8.8 g (19.5 mmol) of (1S,3S)-1-(4-chloro-3-sulfonamidobenzoylamino)methyl-1,2,3,4-tetrahydroisoquinoline-3-carboxylic acid ethyl ester and 2.5 g (24.7 mmol) of triethylamine in 150 ml $CH_2Cl_2$. The reaction is stirred at room temperature overnight, then worked up as in Example 7A. Chromatography of the residue gives the desired product.

B.
Ethyl(1S,3S)-1-(4-chloro-3-sulfonamidobenzoylamino)-methyl-2-((2S)-N-((1S)-1-ethoxycarbonyl-3-phenylpropyl)amino)propionyl-1,2,3,4-tetrahydroisoquinoline-3-carboxylate A solution of 7.5 g (8.3 mmol) of compound 9A in 100 ml EtOH is treated with 25 ml HOAc, followed by 3.5 g (0.054 mol) of zinc dust. The resulting slurry is stirred at room temperature until TLC shows the absence of starting material. The reaction is then filtered and concentrated in vacuo. Chromatography on silica gel gives the pure amine.

C.
(1S,3S)-1-(4-chloro-3-sulfonamidobenzoylamino)methyl-2-((2S)-N-((1S)-1-carboxy-3-phenylpropyl)amino)-propionyl-1,2,3,4-tetrahydroisoquinoline-3-carboxylic acid A solution of 2.7 g (3.7 mmol) of the above diester in 35 ml EtOH is cooled in ice and treated with 20 ml 1N NaOH. The resulting solution is stirred at room temperature. When TLC indicates complete conversion to diacid the mixture is carefully neutralized with dilute acid and concentrated in vacuo. Chromatography of the residue provides the pure diacid.

EXAMPLE 10

A.
1-((2S)-2-(N-((1S)-1-Ethoxycarbonyl-3-phenylpropyl)amino)propionyl)-4-(2,3-dichloro-4-((ethoxycarbonyl)methoxy)benzoyl)methyleneproline ethyl ester The acid chloride from 6.7 g (14.7 mmol) of N-((1S)-1-ethoxycarbonyl-3-phenylpropyl)-N-(2,2,2-trichloroethoxycarbonyl)alanine (Example 7A) is dissolved in 25 ml $CH_2Cl_2$ and added dropwise to a solution of 6.3 g (14.6 mmol) of 4-(2,3-dichloro-4-((ethoxycarbonyl)methoxy)benzoyl)methylene proline ethyl ester and 1.6 g (15.8 mmol) of triethylamine in 100 ml $CH_2Cl_2$. Further reaction and purification as in example 7A gives the desired amide.

This is dissolved in 100 ml EtOH and treated with 25.1 ml HOAc and 6.5 g (0.10 mol) of zinc dust. The reaction is stirred at room temperature until starting material is consumed (TLC), then worked up as described for Example 7B. Careful chromatography on silica gel then gives the pure amine.

B.
1-((2S)-2-(N-((1S)-1-Carboxy-3-phenylpropyl)amino)propionyl)-4-(2,3-dichloro-4-(carboxymethoxy)benzoyl)methyleneproline A solution of 4.7 g (7.5 mmol) of the above triester 10A in 25 ml EtOH is cooled in ice and treated with 10 ml 10% NaOH (0.025 mol). The mixture is stirred until TLC shows complete conversion to triacid, then worked up and purified according to Example 7C to give the desired product.

EXAMPLE 11

1-((2S)-2-(N-((1S)-1-Carboxy-3-phenylpropyl)amino)-propionyl-4-ethoxy-4-(5-chloro-2,4-disulfonamidophenyl)aminoproline 4-Ethoxy-4-(5-chloro-2,4-disulfonamidophenyl)aminoproline ethyl ester (6.7 g, 14.3 mmol) is treated with the acid chloride from 6.6 g (14.5 mmol) of N-((1S)-1-ethoxycarbonyl-3-phenylpropyl)-N-(2,2,2-trichloroethoxycarbonyl)alanine as per Example 7A. Further deprotection (Example 7B) and hydrolysis (Example 7C) as previously described gives the desired product.

What is claimed is:

1. A compound of the formula

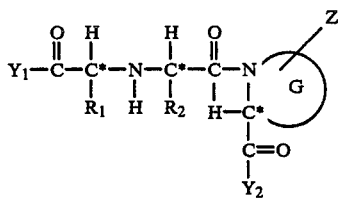

wherein $Y_1$ and $Y_2$ are independently OH or alkoxy having 1 to 8 carbon atoms;

$R_1$ is H, $C_1$-$C_8$-alkyl, phenyl-$C_1$-$C_8$-alkyl or indanyl;

$R_2$ is H, $C_1$-$C_8$-alkyl or amino-$C_1$-$C_8$-alkyl;

$R_3$ is H or $C_{1-8}$ alkyl;

G with the nitrogen and carbon to which it is joined forms a proline,

Z is —(CH$_2$)$_i$—N(R$_3$)SO$_2$—M; =N(CH$_2$)$_i$—SO$_2$—M; —(CH$_2$)$_i$—N(R$_3$)—M; =N(CH$_2$)$_i$—M; =CH—(CH$_2$)$_i$—C(O)—M; or —(CH$_2$)$_i$—N(R$_3$)—C(O)—M;

i is 0 to 6 inclusive;

M is

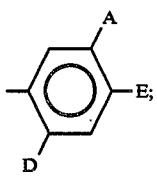

A is SO$_2$NH$_2$ or halogen;

D is SO$_2$NH$_2$ or halogen;

E is SO$_2$NH$_2$, halogen, or NH$_2$ or a pharmaceutically acceptable acid addition, alkali or alkaline earth metal salt.

2. A compound of claim 1 having the formula

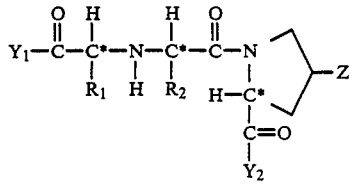

wherein

M is

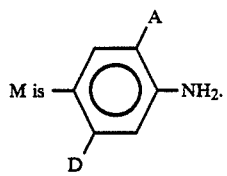

3. The compound according to claim 1 which is N-[N-[(1S)-1-(Hydroxycarbonyl)-3-phenylpropyl]-L-alanyl]-4-(2,4-disulfamoyl-5-chloroanilino)proline or a pharmaceutically acceptable acid addition alkali metal, or alkaline earth metal salt thereof.

4. The compound according to claim 1 which is N-[N-[(1S)-1-(Hydroxycarbonyl)-3-phenylpropyl]-L-alanyl]-4-(2,4-disulfamoyl-5-chlorophenylimino)proline or a pharmaceutically acceptable acid addition alkali metal, or alkaline earth metal salt thereof.

5. The compound according to claim 1 which is N-[N-[(1S)-1-(Hydroxycarbonyl)-3-phenylpropyl]-L-alanyl]-4-(2-chloro-4-amino-5-sulfamoylphenyl-sulfonylimino)proline or a pharmaceutically acceptable acid addition alkali metal, or alkaline earth metal salt thereof.

6. The compound according to claim 1 which is (4S)-1-((2S)-2-(N-((1S)-1-Carboxy-3-phenylpropyl)amino)-propionyl)-4-(4-amino-2-chloro-5-sulfonamidobenzenesulfonyl)aminoproline or a pharmaceutically acceptable acid addition, alkali metal, or alkaline earth metal salt thereof.

7. An antihypertensive pharmaceutical preparation comprising a compound or salt according to claim 1 and a pharmaceutically acceptable carrier.

8. An anti-glaucoma pharmaceutical preparation comprising a compound or salt according to claim 1 and a pharmaceutically acceptable carrier.

9. A method of relieving hypertension in a host suffering therefrom, comprising administering to said host a therapeutically effective amount of a compound or salt according to claim 1.

10. A method of relieving elevated intraocular pressure in a host suffering therefrom, comprising administering to said host a therapeutically effective amount of a compound or salt according to claim 1.

* * * * *